(12) United States Patent
Bergquist et al.

(10) Patent No.: US 7,504,207 B2
(45) Date of Patent: Mar. 17, 2009

(54) RANDOM DRIFT MUTAGENESIS

(75) Inventors: Peter Leonard Bergquist, Auckland (NZ); Moreland David Gibbs, Turramurra (AU); Rosalind Reeves, Turramurra (AU)

(73) Assignee: Macquarie University, North Ryde, NSW (AU)

( * ) Notice: Subject to any disclaimer, the term of this patent is extended or adjusted under 35 U.S.C. 154(b) by 19 days.

(21) Appl. No.: 10/530,314

(22) PCT Filed: Oct. 7, 2003

(86) PCT No.: PCT/AU03/01314

§ 371 (c)(1),
(2), (4) Date: Dec. 8, 2006

(87) PCT Pub. No.: WO2004/031387

PCT Pub. Date: Apr. 15, 2004

(65) Prior Publication Data

US 2007/0275443 A1    Nov. 29, 2007

(30) Foreign Application Priority Data

Oct. 4, 2002    (AU)  ............................... 2002951899

(51) Int. Cl.
*C12Q 1/68* (2006.01)
(52) U.S. Cl. ......................................................... 435/6
(58) Field of Classification Search ..................... 435/6
See application file for complete search history.

(56) References Cited

U.S. PATENT DOCUMENTS 6,323,030 B1    11/2001 Stemmer

FOREIGN PATENT DOCUMENTS

WO    WO 99/20768    4/1999
WO    WO 02/18629 A1    3/2002

OTHER PUBLICATIONS

Rice et al. PNAS, vol. 89, pp. 5467-5471, Jun. 1992.*
Cadwell, et al. 1992. Randomization of genes by PCR mutagenesis. *PCR Methods and Applications*, 2:28-33.
Coco, et al. 2001. DNA shuffling method for generating highly recombined genes and evolved enzymes. *Nature Biotechnology*, 19:354-359.
Cohen, et al. 2001. In vitro enzyme evolution: The screening challenge of isolating the one in a million. *Trends in Biotechnology*, 19(12):507-510.
Farinas, et al. 2001. Directed Enzyme Evolution. *Current Opinion in Biotechnology*, 12:545-551.
Gibbs, et al. 1995. Cloning, sequencing and expression of a xylanase gene from the extreme thermophile Dictyoglomus thermophilum Rt46B.1 and activity of the enzyme on fiber-bound substrate. *Applied and Environmental Microbiology*, 61(12):4403-4408.
Gibbs, et al. 2001. Degenerate oligonucleotide gene shuffling (DOGS): A method for enhancing the frequency of recombination with family shuffling. *Gene*, 271:13-20.
Joo, et al. 1999. Laboratory evolution of peroxide-mediated cytochrome P450 hydroxylation. *Nature*, 399:670-673.
Joo, et al. 1999. A high-throughput digital imaging screen for the discovery and directed evolution of oxygenases. *Chemistry & Biology*, 6(10):699-706.
Kikuchi, et al. 1999. Novel family shuffling methods for the in vitro evolution of enzymes. *Gene*, 236:159-167.
Love, et al. 1988. Sequence structure and expression of a cloned β-glucosidase from an extreme thermophile. *Mol Gen Genet*, 213:84-92.
Morris, et al. 1998. Cloning of the *xynB* gene from Dictyoglomus thermophilum Rt46B.1 and action of the gene product on kraft pulp. *Applied and Environmental Microbiology*, 64(5):1759-1765.
Ostermeier, et al. 1999. A combinatorial approach to hybrid enzymes independent of DNA homology. *Nature Biotechnology*, 17:1205-1209.
Shibuya, et al. 2000. Enhancement of the thermostability and hydrolytic activity of xylanase by random gene shuffling. *Biochem. J.*, 349:651-656.
Stemmer, W. P. C. 1994. Rapid evolution of a protein in vitro by DNA shuffling. *Nature*, 370:389-391.
Stemmer, W. P. C. 1994. DNA shuffling by random fragmentation and reassembly: In vitro recombination for molecular evolution. *Proc. Natl. Acad. USA*, 91:10747-10751.
Zhang, et al. 1997. Directed evolution of a fucosidase from a galactosidase by DNA shuffling and screening. *Proc. Natl. Acad. Sci. USA*, 94:4504-4509.
International Search Report from PCT/AU03/01314 dated Nov. 17, 2003.
International Preliminary Examination Report from PCT/AU2003/001314 dated Jan. 21, 2005.

(Continued)

*Primary Examiner*—Kenneth R. Horlick
*Assistant Examiner*—Cynthia B Wilder
(74) *Attorney, Agent, or Firm*—Knobbe, Martens, Olson & Bear, LLP

(57) ABSTRACT

A method for producing a mutant gene encoding a functional gene product comprising: (a) introducing one or more mutations into a gene to form a mutated gene; (b) providing the mutated gene to a host microorganism; (c) culturing the host microorganism containing the mutated gene under conditions which allow expression of the mutant gene product; and (d) selecting a host microorganism capable of producing a functional gene production from the mutated gene.

15 Claims, 5 Drawing Sheets

OTHER PUBLICATIONS

Bergquist, et al. 2002. Degenerate oligonucleotide gene shuffling (DOGS) and random drift mutagenesis (RNDM): Two complementary techniques for enzyme evolution. *Biomolecular Engineering*, 22:63-72.

Bornscheuer, U. T. 2001. Directed evolution of enzymes for biocatalytic applications. *Biocatalysis and Biotransformation*, 19:85-97.

Chirumamilla, et al. 2001. Improving the quality of industrially important enzymes by directed evolution. *Molecular and Cellular Biochemistry*, 224:159-168.

Matsumura, et al. 2001. In vitro evolution of beta-glucuronidase into a beta-galactosidase proceeds through non-specific intermediates. *J. Mol. Biol.*, 305:331-339.

Supplementary European Search Report from EP 03 74 7711 dated Mar. 16, 2006.

* cited by examiner

RANDOM DRIFT MUTAGENESIS

CROSS-REFERENCE TO RELATED APPLICATIONS

This is the U.S. National Phase under 35 U.S.C. § 371 of International Application No. PCT/AU2003/001314, filed Oct. 7, 2003 and published in English on Apr. 15, 2004, which claims priority to Australian Patent Application No. 2002 951899, filed Oct. 4, 2002.

TECHNICAL FIELD

The present invention is directed to methods for producing mutant genes and mutant gene products.

BACKGROUND ART

There are many situations such as medical, veterinary and industrial applications, where mutant gene products are desirable. Microorganisms can produce a great variety of proteins, particularly enzymes, which can be used in may situations. Many of these proteins, however, have characteristics that are not ideal for subsequent use and therefore it is desirable to obtain mutants with altered activity or functions. There are a number of methods and techniques presently in use which can generate mutant genes and corresponding mutant gene products.

Stemmer (Stemmer, W. P. C. Rapid evolution of a protein in vitro by DNA shuffling. *Nature* 370, 389-391, 1994; Stemmer, W. P. C. DNA shuffling by random fragmentation and reassembly: in vitro recombination for molecular evolution. *Proc. Natl. Acad. USA* 91; 10747-10751, 1994) has discussed the most effective methods to search sequence space in vitro to yield the greatest diversity of protein variants. Until recently, the most popular methods of creating combinatorial libraries are recursive strategies that seek to evolve sequences by the addition of point mutations (Cadwell and Joyce. Randomization of genes by PCR mutagenesis. *PCR Methods Appl.* 2: 28-33, 1992). For in vitro evolution, inclusion of recombinant polymerase chain reaction PCR (gene shuffling) offers practical and theoretical advantages over simple recursive point mutagenesis methods. It will rapidly fine tune the mutational load in several parts of the protein by recombining point mutations and wild-type sequences. The technique (and its variations) have been used to enhance enzyme activity, substrate specificity and stability. Gene shuffling is usually achieved by fragmentation of the genes to be shuffled followed by PCR. This method relies on homologous recombination during the PCR reassembly step. Most methods require relatively high levels of sequence similarity between the genes to be shuffled as 'cross-over points' appear to occur in these regions.

If sequence similarity is low between the input genes, the majority products tend to be the reassembled parental genes and extensive searches need to be carried out to find recombinants (Kikuchi, M., Ohnishi, K. & Harayama, S. Novel family shuffling methods for the In vitro evolution of enzymes. *Gene* 236, 159-167, 1999; Ostermeier, M., Shim, J. H. & Benkovic, S. J. A combinatorial approach to hybrid enzymes independent of DNA homology. *Nat. Biotechnol.* 17, 1205-1209, 1999). Kichuchi et al (1999) have reported on methods for gene shuffling that make use of unique restriction enzyme sites in the sequences of the parental molecules and following cleavage, several PCR steps were carried out to amplify the recombinant genes, a process that allowed hybrid genes to be formed at high frequency.

An entirely different procedure was proposed by Ostermeier et al (1999) that allowed the preparation of combinatorial fusion libraries by progressive truncation of coding sequences of the two parental sequences followed by ligation of the fragments and selection for enzyme activity. Either parent can be used to provide 5' sequence for the hybrid gene. This procedure, termed iterative truncation for the creation of hybrid enzymes (ITCHY), can accommodate recombination between genes with as little as 50% sequence similarity and was found to give a wider range of crossovers compared with standard gene shuffling techniques.

The present applicant has isolated a gene coding for a thermophilic beta-xylanase that had improved performance in the bleaching of paper pulp. It was desired to investigate the possibility of obtaining mutant derivatives that had enhanced stability and an altered pH optimum. Experiments using error-prone PCR and mis-incorporation mutagenesis followed by gene shuffling allowed the identification of mutant genes that coded for a limited sample of the variations in sequence space but required extensive screening for their identification. Gene shuffling following DNAseI fragmentation of related genes (family shuffling) overwhelmingly gave wild type parental sequences as the major products. After several trials of methods designed to reduce the background, a technique was devised that allows shuffling of genes that differ widely in sequence similarity and G:C content and greatly reduces the appearance of wild type genes. Furthermore, the primer extension conditions may be modified to bias the resulting progeny genes towards any one (or more) of the parental input genes. The present applicant termed this procedure Degenerate Oligonucleotide Gene Shuffling (DOGS) which is described in WO 02/18629.

Although there are many options available to generate mutants, those methods do not necessarily result in useful products or may be too time consuming or unsuccessful. The present inventors have now developed a new method capable of producing potentially many different functional mutants.

DISCLOSURE OF INVENTION

In a first aspect, the present invention provides a method for producing a mutant gene encoding a functional gene product, the method comprising:
(a) introducing one or more mutations into a gene to form a mutated gene;
(b) providing the mutated gene to a host microorganism;
(c) culturing the host microorganism containing the mutated gene under conditions which allow expression of the mutant gene product; and
(d) selecting a host microorganism capable of producing a functional gene product from the mutated gene.

In a preferred form, the method comprises:
(a) introducing one or mutations into a gene to form a plurality of mutated genes;
(b) providing the mutated genes to host microorganisms;
(c) culturing the host microorganisms containing the mutated genes under conditions which allow expression of the mutant gene products; and
(d) selecting host microorganisms capable of producing a functional gene product from a mutated gene.

In a preferred form, the method further comprises:
(e) obtaining a combined pool of mutated genes encoding functional gene products from the microorganisms in step (d) and repeating steps (a) to (d) to form a library of microorganisms containing a plurality of mutant genes capable of being expressed and producing functional gene products.

In another preferred form, the method further comprises:
(f) screening the library of microorganisms to obtain a mutant gene capable of expressing a mutant gene product.

Preferably, the mutant gene product has an altered or desired activity, function, or characteristic compared with the native gene product.

Preferably, step (a) is carried out by mis-incorporation mutagenesis using polymerase chain reaction (PCR). It will be appreciated, however, that other methods known to the art to introduce one or mutations into a gene would also be suitable. An example includes, but is not limited to, gene shuffling.

Preferably, step (b) is carried out by ligating the mutant gene into a vector and transforming a bacterium with the vector. Methods of introducing gene(s) into microorganisms are well known to the art and would be applicable for the present invention. The vector may be a plasmid or virus, for example. A microorganism particularly suitable for this step in the bacterium *Escherichia coli*. It will be appreciated that other host microorganisms could also be used for this step.

Preferably, the host microorganisms are cultured under conditions in which the native gene would be expected to be expressed in the particular host microorganism. Liquid culture is particularly suitable for this step as it allows easy retrieval of the cultured microorganisms for subsequent use or analysis. It will be appreciated, however, that any suitable culturing means can be used in this step such as those found in Morris et al. Cloning of the xynB gene from *Dictyoglomus thermophilum* strain Rt46B.1 and action of the gene-product on kraft pulp. *Appl. Environ. Microbiol.* 64:1759-1765, 1998; Gibbs et al. Cloning, sequencing and expression of a xylanase gene from the extreme thermophile *Dictyoglomus* Rt46B.1 and the activity of the enzyme on fibre-bound substrate. *Appl. Environ. Microbiol.* 61:4403-4408, 1995 (incorporated herein by reference).

In a further preferred form, the culture conditions result in any host microorganism capable of expressing a functional gene having a detectable characteristic. One preferred form of a detectable characteristic is a selectable phenotype. Examples include colour, size, shape, fluorescence, dependency on a supplied metabolite for growth, enzymatic activity such as enzymatic conversion of a supplied substrate which would allow selection based upon colour or fluorescence. In a more preferred form, the gene encodes an enzyme that can form a fluorometric or chromogenic phenotype or character in a microorganism expressing the gene preferably under appropriate conditions.

In a more preferred form, the gene encodes an enzyme which can form a fluorometric or chromogenic phenotype or character in a microorganism expressing the gene under liquid culture conditions.

The present invention is particularly suitable for high volume screening using a sorting or selecting instrument such as a cell sorter or cytometer. Many different enzymes can act on a substrate to produce a coloured product. When the substrate is acted upon in a cell, the cell may change colour which is then detectable. Accordingly, under the appropriate cultural conditions, microorganisms which express a functional gene product will be coloured and therefore selectable over other microorganisms which do not produce a functional product.

A difference between the present invention and other methods for obtaining mutant genes is that it does not apply any selective pressure or testing for altered activity of the mutant gene products during the process, apart from the retention of function by the mutated gene product.

A further difference between the present invention and other methods for obtaining mutant genes is that it does not select for the removal of neutral mutations or mutations which reduce but do not eliminate the function of the mutated gene product.

The method according to the present invention can be used to produce potentially a large number of different mutant genes encoding functional gene products with potentially large numbers of mutations which can then be tested for altered characteristics or desired qualities or function.

In a preferred form, the gene product is an enzyme. More preferably, the enzyme is capable of acting on an X-sugar or a fluorescein-linked sugar such as Imagene Green ($C_{12}$FDG, Molecular Probes, Eugene, Oreg., USA). The enzyme is preferably capable of acting on a substrate such as X-gal which forms a chromogen upon enzymatic hydrolysis, X-gal being defined as 5-Bromo-4-chloro-3-indolyl-D-galactopyranoside.

In a further preferred form, the gene product substrate should be retained on, or within the cell, in liquid culture.

In a second aspect, the present invention provides a mutant gene capable of producing a mutant gene product produced by the method according to the first aspect of the present invention.

In a third aspect, the present invention provides a method for producing a mutant gene encoding a functional enzyme, the method comprising:
(a) introducing one or more mutations into a gene encoding the enzyme to form a plurality of mutated genes;
(b) incorporating the mutated genes into vectors;
(c) transforming host microorganisms with the vectors;
(d) culturing the host microorganisms containing the mutated genes under conditions which would allow expression of the corresponding native gene to produce the native enzyme such that the microorganisms express the mutant genes;
(e) providing a substrate upon which the enzyme can act to produce a selectable phenotype in any host bacterium producing a functional enzyme; and
(f) selecting host microorganisms capable of producing a functional gene product from the mutated gene by sorting bacteria having the selectable phenotype.

In a preferred form, the method further comprises:
(g) obtaining a pool of mutated genes from the microorganisms in step (f) and repeating steps (a) to (f) to form a library of microorganisms containing a plurality of multiply-mutant genes capable of being expressed and producing functional enzymes.

In another preferred form, the method further comprises:
(h) screening the library of microorganisms to obtain a mutant gene capable of expressing an enzyme with an altered or desired activity, function, or characteristic.

Preferably, the microorganisms are bacteria. A suitable bacterium is *Escherichia coli*, although other suitable host bacteria can be used.

Preferably the sorting is done by fluorescence activated cell sorting (FACS) using flow-cytometry and the bacteria selected by changes in their spectral or fluorescence characteristics due to action of the functional enzyme on the substrate.

In a fourth aspect, the present invention provides a mutant gene capable of producing a mutant gene product produced by the method according to the third aspect of the present invention.

In a fifth aspect, the present invention provides a method for obtaining a mutant or chimeric gene comprising:
(a) to (f) carrying out the steps according to the first aspect of the present invention to obtain a mutant gene;
(g) providing the mutant gene to a host microorganism; and (h) carrying out a further mutagenic step to obtain a mutant or chimeric gene.

It will be appreciated that any suitable mutagenic process in step (h) would be suitable. Examples include, but not limited to, gene shuffling or degenerate oligonucleotide gene shuffling, or mutagenic polymerase chain reaction (PCR).

In a preferred embodiment, step (h) comprises:
(i) assigning one or more segments of the mutant gene based on regions of shared encoded amino acid sequence;
(ii) amplifying the one or more assigned segments of the gene using a primer having a non-degenerate core based on a segment or template of a gene to be amplified, and the core being flanked by both 5' and 3' ends which, if required, are degenerate; and
(iii) causing recombination of the one or more amplified segments to form a mutant or chimeric gene.

In a sixth aspect, the present invention provides a mutant or chimeric gene produced by the method according to the fifth aspect of the present invention.

In a seventh aspect, the present invention provides a method for obtaining a mutant or chimeric gene encoding an enzyme, the method comprising:
(a) to (h) carrying out the steps according to the third aspect of the present invention to obtain a mutant gene encoding an enzyme;
(i) providing the mutant gene to a host microorganism; and
(j) carrying out a further mutagenic step to obtain a mutant or chimeric gene encoding an enzyme.

It will be appreciated that any suitable mutagenic process in step (j) would be suitable. Examples include, but not limited to, gene shuffling or degenerate oligonucleotide gene shuffling, or mutagenic PCR (Gibbs et al. Degenerate oligonucleotide gene shuffling (DOGS): A method for enhancing the frequency of recombination with family shuffling *Gene* 271: 13-20, 2001. A review of other suitable directed evolution methods can be found in Farinas et al. Directed Enzyme Evolution. *Current Opinion in Biotechnology* 12: 545-551, 2001 (incorporated herein by reference).

In a preferred embodiment, step A) comprises:
(i) assigning one or more segments of the mutant gene based on regions of shared encoded amino acid sequence;
(ii) amplifying the one or more assigned segments of the gene using a primer having a non-degenerate core based on a segment or template of a gene to be amplified, and the core being flanked by both 5' and 3' ends which, if required, are degenerate; and
(iii) causing recombination of the one or more amplified segments to form a mutant or chimeric gene encoding an enzyme.

In an eighth aspect, the present invention provides a mutant or chimeric gene encoding an enzyme produced by the method according to the seventh aspect of the present invention.

The methods according to the present invention are particularly applicable to the directed evolution of any gene/enzyme capable of hydrolysing a synthetic target substrate with fluorogenic properties.

The substrate could be any indoxyl-linked compound. However, any other chromogenic or fluorogenic substrate that is retained in the cell subsequent to hydrolysis, and can be detected by flow cytometry or other means, would be suitable.

Many indoxyl-linked substrates are commercially available as substrates for many glycosyl hydrolases, including, cellulases, beta-glucosidases, beta-galactosidases, mannosidases, xylanases and beta-xylosidases. Substrates are also available for esterases and/or lipases.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the present invention may be more clearly understood, preferred forms will be described with reference to the following drawings and examples.

A. Sorting of *E. coli* cell populations containing either the plasmid pProEXHTc:bglA or pProEXHTc in the presence or absence of the chromagenic substrate X-gal. Key:
Red: Cells expressing BglA in the presence of X-gal
Blue: Cells expressing BglA in the absence of X-gal
Green: Control cells (vector only) in the presence of X-gal
Magenta: Control cells (vector only) in the absence of X-gal B. Part 1. Overlayed datasets from part A showing the clear delineation between cell populations expressing the BglA+ phenotype (red) vs BglA− phenotype (green). Parts 2 and 3. Overlayed datasets from part A showing that presence or absence of X-gal did not contribute to observed effects. The data shows that this Indigo precipitate can be detected within *E. coli* by FACS techniques.

Figure 4:
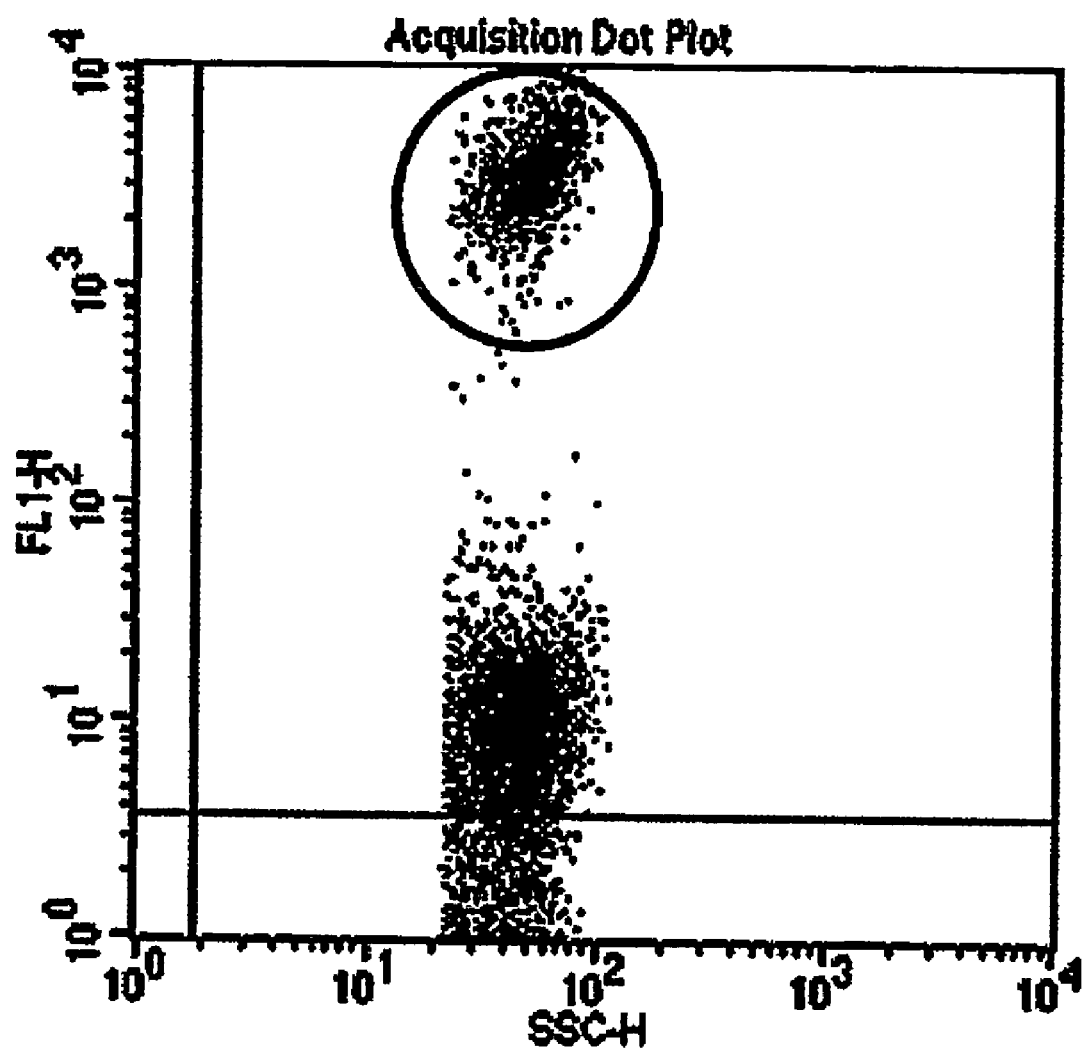

FIG. 4. Showing cell population sorting by FACS flow cytometry (excitation 488, emission FL1 515-565 nm) based upon expression of BglA phenotype and accumulation of Imagene Green within the BglA+ cells. The results show a clear delineation of cell populations expressing the BglA+ phenotype (circled) vs BglA− phenotype (uncircled) based upon cell fluorescence due to the hydrolysis of Imagene Green within each cell by BglA.

Figure 5:

FIG. 5. Epi-fluorescence microscopy of DH5-alpha cells transformed with pProEXHTc:bglA (BglA+) following a 5 minute 65° C. heat shock in the presence of Imagene green.

MODE(S) FOR CARRYING OUT THE INVENTION

The present inventors have developed a new procedure for achieving directed evolution of proteins, particularly enzymes, which are more suited to novel environments and applications than their natural counterparts. The method is particularly adaptable for utilising flow cytometry and chromogenic or fluorogenic substrates. The method allows repeated rounds of in vitro mutation and recombination between selected mutants, followed by screening for isolates with an altered pH optimum for activity and selection of the most fit survivors. One particular use resulted in the isolation of novel glycosyl hydrolases with superior enzymatic specifications, their expression, and evaluation for their industrial potential, i.e. pH suitability.

The present applicant has also developed a novel method for the in vitro evolution of proteins called Degenerate Oligonucleotide Gene Shuffling (DOGS) (WO 02/18629, incorporated herein by reference). The DOGS method was designed for shuffling genes from different families, but it has now been found that it is applicable to random mutations of a single gene so that the limits of sequence space can be explored. This is performed by mis-incorporation mutagenesis during PCR synthesis of a copy of the target gene. The iterative screening of mis-incorporation mutagenesis libraries with low mutation frequencies (1-2 amino acid changes/protein) allows the stepwise accumulation of adaptive mutations. Stepwise accumulation of single mutations allows the sampling of a far larger functional sequence space than if highly mutated recombinants are screened. As a consequence, mis-incorporation mutagenesis tends to select for adaptive mutations while discarding neutral mutations or mutations which decrease the fitness of an enzyme.

Phenotypes such as thermostability can be readily improved by iterative incorporation of single mutations. The present inventors have developed a technique to determine whether a phenotype that is derived from the interaction of multiple amino acids (in this case, an enzyme's pH optimum) might require the accumulation and interaction of neutral mutations (neutral in isolation), and adaptive mutations. A preferred form of the method according to the present invention uses iterative mis-incorporation mutagenesis in the normal manner. However, no screening for adaptive mutations occurs or is required. Instead, screening is only done for retained ability (whether unchanged, improved or reduced) to catalyse the hydrolysis of a substrate. All positive recombinants would be combined and used as template for a further round of mutagenesis and so on for as many rounds as are necessary. In this manner, it is assumed that accumulation of multiple adaptive, neutral and harmful (but not inactivating) mutations would occur. Once generated, this library can then be screened for enzymes with modified pH optima, for example. Recombinants with the desired phenotype optionally can then be backcrossed with the parental wild-type gene using DOGS to remove any mutations not contributing to the altered phenotype.

Procedure

Figure 1:
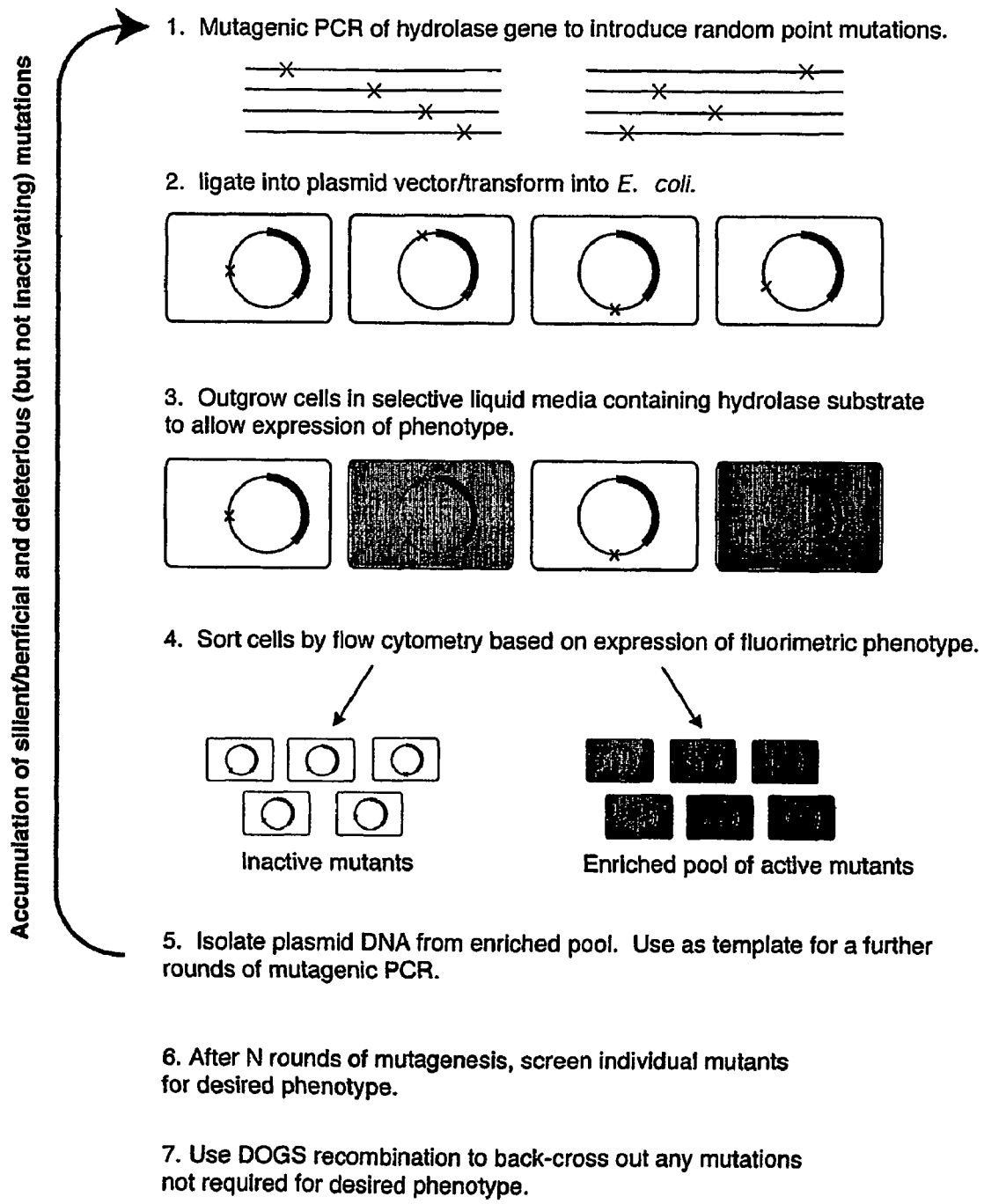
FIG. 1. Random Drift flow diagram outlining the basic concept of random drift mutagenesis.

FIG. 1 shows a schematic of a method for random drift mutagenesis according to the present invention. Step 1 involves mutagenic PCR of a number of copies of a gene encoding an enzyme to form a plurality of mutant genes. The mutated genes are then ligated into plasmids and transformed into *E. coli*. The bacteria are then cultured in selective media that contains a substrate which, when acted upon by any functional enzyme in the cell will cause the cell to have a detectable phenotype. The cultured cells are then sorted by a flow cytometer and cells having the phenotype induced by the enzyme are selected. All selected cells will contain a gene encoding a functional enzyme. Plasmid DNA can be obtained from any of the cells and processed again through the method to obtain further mutants. After a number of rounds of mutagenesis and cell selection, individual mutants can be screen for enzymes having a desired or altered characteristic. The mutants can be further mutated or crossed by other means.

EXAMPLES

The experiment used the gene for a thermostable enzyme and a relatively inexpensive substrate. The method was also be applied it to the gene for *Dictyoglomus* XynB enzyme (Morris et al. Cloning of the xynB gene from *Dictyoglomus thermophilum* strain Rt46B.1 and action of the gene-product on kraft pulp. *Appl. Environ. Microbiol.* 64:1759-1765, 1998) that is a candidate in the pulp bleaching area (and would use a custom-synthesized substrate in the mutagenesis experiments).

Experimental and Techniques

Gene: *Caldicellulosiruptor saccharolyticus* β-glucosidase, bglA (Love et al. Sequence structure and expression of a cloned β-glucosidase from an extreme thermophile. *Mol Gen Genet.* 213: 84-92, 1988); Substrate: β-D-chloroindolyl-galactoside (X-gal) or β-D-chloroindolyl-glucose (X-glu). Cleavage of these commercial substrates by hydrolases such as BglA results in the precipitation of insoluble indigo, in our case, inside the cell. For all experiments the bglA gene was ligated in-frame into the expression vector pProEXHTc (Invitrogen, CA, USA) and transformed into *E. coli* DH5-alpha. Detectable levels of BglA gene product were produced using the substrates X-gal and $C_{12}$FDG. No induction with IPTG was required due to low levels of constitutive expression from the pProEXHTc TAC promoter.

Steps:
(i) PCR mutagenesis of BglA gene to give 1-2 changed amino acids per recombinant gene (Cadwell and Joyce. Randomization of genes by PCR mutagenesis. *PCR methods Appl* 2: 28-33, 1992). Mutagenic PCR was achieved using 5 units Amplitaq (Perkin Elmer), a final concentration of 1× Amplitaq PCR buffer, 7 mM $MgCL_2$, 0.2 mM dGTP, 0.2 mM dATP, 1 mM dCTP, 1 mM dTTP, 0.5 mM $MnCl_2$, 0.2 μM forward primer, 0.2 μM reverse primer, and 0.1 ng bglA template in a final volume of 50 μl.
(ii) Ligate mutagenic PCR product into vector and transform into Δlac host. The restriction sites NcoI and BamHI were incorporated into the forward and reverse primers respectively to allow restriction digest of the bglA PCR product, and directional ligation into pProEXHTc predigested with the same restriction enzymes. Ligation mixtures were transformed into highly competent *E. coli* DH5-alpha ($5×10^8$ cfu/μg DNA, Invitrogen).
(iii) Outgrow transformation mix in LB+ X-gal (0.2 mg/ml)+ Ampicillin (60 μg 1 ml) to allow expression of BglA and hydrolysis of X-gal. Sort cells by FACS flow cytometry into those containing indigo (BglA+), and those without (BglA−) by detection of emission at 515-565 nm.
(iv) Take BglA+ cells, release plasmid DNA by heating cells at 95° C. for 15 minutes.

(v) Go to step (i) and repeat. Use released plasmid DNA as template for next round of mutagenic PCR.

(vi) At the end of each round, plate a portion of the recombinants, check they are still active (check also ratio of +ve to −ve to confirm sorting procedure) and sequence some recombinants to determine level of accumulation of mutations.

Steps (i) to (vi) usually can be done in 1 to 2 days. This technique allows selection from about $10^6$ potential mutants at each round of cell sorting. If only 10% of single point mutation mutants retain activity, then potentially $10^5$ mutants can be sorted and retained at each round. This method allows the rapid selection of recombinants with multiple mutations and eliminates tedious screening procedures.

The present inventors have found that the fluorescent beta-galactosidase/beta-glucosidase substrate Imagene Green ($C_{12}FDG$, Molecular Probes, USA) is a good substrate for flow cytometry detection of *E. coli* cells expressing the BglA+ phenotype. This substrate can be directly substituted for X-gal in the examples of the methods according to the present Invention.

Figure 2:
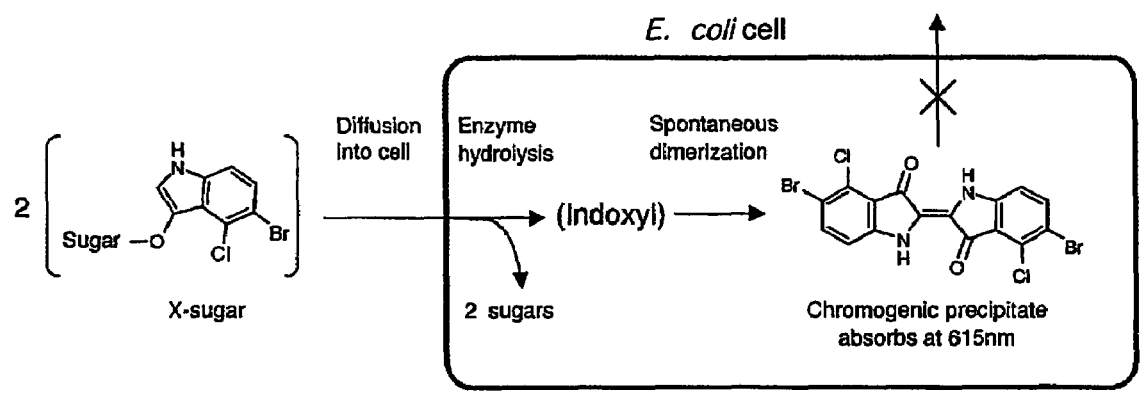
FIG. 2. X-sugar detailing the diffusion of a substrate-linked indoxyl such as X-gal into *E. coli*, followed by enzymatic cleavage to form an insoluble chromogenic Indigo precipitate within the cell.

The present inventors have shown that the hydrolysis product of X-gal can be used to sort cells based upon the accumulation of indigo within those cells expressing the BglA+ phenotype. FIG. 2 shows the chemical reaction by enzymatic hydrolysis of the chromogenic substrate in the cell causing a color change to the bacterial cell with a functional enzyme.

Figure 3:
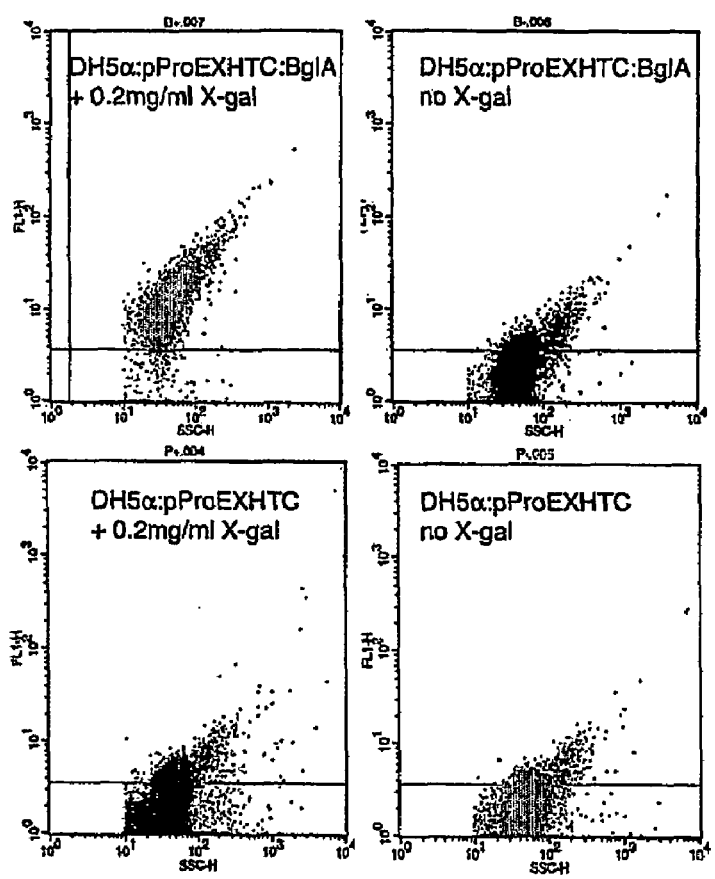
FIG. 3. Flow diagram of cell sorting by FACS flow cytometry (excitation 488, emission FL1 515-565 nm) based upon expression of BglA phenotype and accumulation of insoluble Indigo within *E. coli* DH5-alpha cells containing the plasmid pProEXHTc:bglA.
Figure 3:
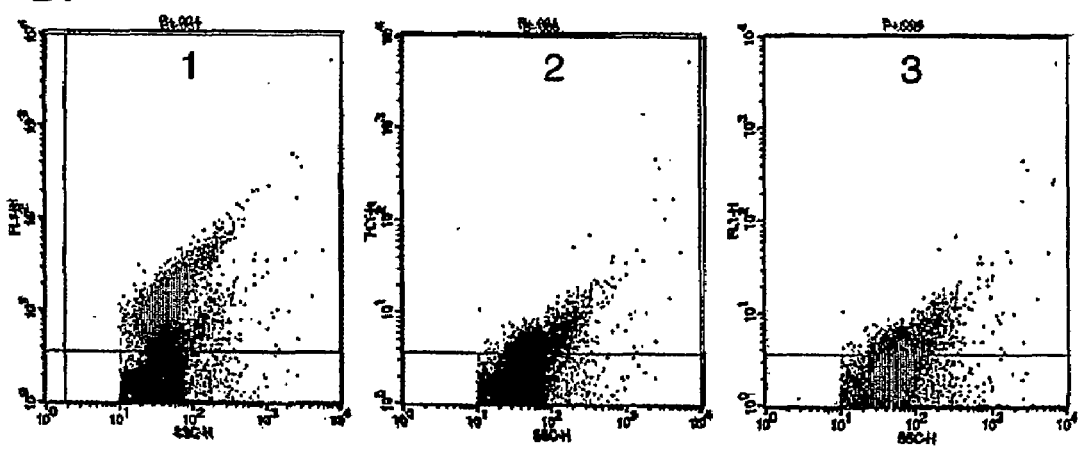

FIG. 3 shows that these indigo-labelled cells can be readily distinguished from unlabelled cells using a Becton Dickinson FACS Calibur Flow cytometry system employing an Argon ion 488 nm laser, using the FL1 emission filter (515-565 nm).

FIG. 4 shows cell population sorting by FACS flow cytometry (excitation 488, emission FL1 515-565 nm) based upon expression of BglA phenotype and accumulation of Imagene Green within the BglA+ cells. The results show a clear delineation of cell populations expressing the BglA+ phenotype (circled) vs BglA− phenotype (uncircled) based upon cell fluorescence due to the hydrolysis of Imagene Green within each cell by BglA.

Furthermore, the present inventors have found that fluorescent labelling of BglA+ cells in the presence of Imagene Green was significantly enhanced if the cells were heated to 65° C. for 5 minutes in the presence of the Imagene green substrate. In this case, DH5-alpha cells transformed with pProEXHTa:bglA Were outgrown in LB+ Ampicillin (60 μg/ml) for approximately 10 hours. Cells were harvested by centrifugation, then resuspended in water containing 10 μM Imagene green, and heated to 65° C. for 5 minutes in waterbath. Cells were then centrifuged, and the pellet resuspended in water without substrate. FIG. 5 shows an epi-fluorescence microscope image (Axioskop 2 microscope, Zeiss, Germany, excitation 450-490 nm) of BglA+ *E. coli* cells labelled with Imagene Green. The observed fluorescence is due to the hydrolysis of Imagene green that has diffused into the cell. Heating of the cells is presumed to reduce the membrane potential of the *E. coli* cell wall allowing rapid diffusion of imagene Green into the cell where it can then be hydrolysed by BglA.

Outcomes

Potentially any substrate that can accumulate within a cell and be detected by fluorescence could be used for sorting. All of the X-substrates such as X-gal and X-glu could be used as they accumulate as indigo within cells. Potentially, we could have X-xylobiose synthesised (X-cellobiose is commercially available so this is technically feasible) to use in xylanase mutagenesis for further improvement of the performance of XynB from *Dictyoglomus thermophilum*. Potentially, many sugars could be labelled with fluoroscein in the manner of Imagene Green for use for random drift mutagenesis. Currently substrates have been synthesised for beta-glucuronidases (FDGlcU, Molecular Probes), beta-glucosidases (FDGlu, Molecular Probes) and glucocerebrosidases (BIODIPY FL $C_{12}$-glucocerebroside, Molecular Probes) Potentially, fluorescein labelled xylobiose could be synthesized to be used in xylanase mutagenesis for further improvement of the performance of XynB from *Dictyoglomus thermophilum* in wood pulp bleaching applications where enzymes must function under high temperature and highly alkaline conditions (Morris et al. Cloning of the xynB gene from *Dictyoglomus thermophilum* strain Rt46B.1 and action of the gene-product on kraft pulp. *Appl. Environ. Microbiol.* 64:1759-1765, 1998). Furthermore, many other carbohydrate degrading enzymes which are already used in commercial processes, including mannanases, dextranases, pullulanases and amylases, may be suitable candidates for improvement by random drift mutagenesis if fluoroscein-linked substrates can be synthesised.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method for producing mutant genes encoding an enzyme, comprising:
   (a) introducing mutations into individual copies of a gene to form a plurality of mutated genes, wherein each mutated gene encodes a mutated enzyme;
   (b) providing the mutated genes to host bacteria by inserting the mutated genes into vectors and transforming the bacteria with the vectors;
   (c) culturing the host bacteria containing the vectors in the presence of a substrate for the enzyme under conditions suitable for activity of the enzyme such that a bacterium expressing a functional enzyme from a mutated gene has a detectable characteristic;
   (d) sorting host bacteria having the detectable characteristic by flow cytometry, wherein the host bacteria are sorted without selecting for an altered or defined level of enzyme activity compared with a corresponding wild type enzyme; and
   (e) obtaining a pool of mutated genes encoding functional enzymes from the bacteria in step (d) and repeating steps (a) to (d) to form a library of bacteria containing a plurality of mutant genes expressing a functional enzyme.

2. The method according to claim 1 further comprising:
   (f) recovering the vectors from the host bacteria expressing a functional enzyme.

3. The method according to claim 2 further comprising:
   (g) screening the library of bacteria to obtain a mutant gene encoding a functional enzyme.

4. The method according to claim 1 wherein step (a) is carried out by mis-incorporation mutagenesis using polymerase chain reaction (PCR) or gene shuffling.

5. The method according to claim 1 wherein the vector is a plasmid or virus.

6. The method according to claim 1 wherein the bacterium is *Escherichia coli*.

7. The method according to claim 1 wherein host bacteria are cultured in a liquid medium.

8. The method according to claim 1 wherein the enzyme forms a fluorometric or chromogenic phenotype or character in the host bacteria.

9. The method according to claim 8 wherein the host bacteria are selected by changes in their spectral or fluorescence characteristics due to action of the enzyme on the substrate.

10. The method according to claim 9 wherein the enzyme is capable of acting on a 5-bromo-4-chloro-3-indolyl-linked sugar substrate or a fluorescein-linked sugar substrate.

11. The method according to claim 10 wherein the substrate is an indolyl-linked compound.

12. The method according to claim 11 wherein the enzyme acting on an indolyl-linked substrate is selected from the group consisting of glycosyl hydrolases, cellulases, beta-glucosidases, beta-galactosidases, mannosidases, xylanases, and beta-xylosidases.

13. The method according to claim 12 wherein the enzyme is capable of acting on 5-Bromo-4-chloro-3-indolyl-D-galactopyranoside which forms a chromogen upon enzymatic hydrolysis.

14. The method according to claim 1 wherein the enzyme substrate is retained on or within the bacteria in liquid culture.

15. The method according to claim 1 wherein the flow cytometry is fluorescence activated cell sorting (FACS).

* * * * *